(12) United States Patent
Barnes et al.

(10) Patent No.: US 9,797,917 B2
(45) Date of Patent: Oct. 24, 2017

(54) CONTACT SENSING PROBE AND METHODS OF USE FOR MICROPLATE LIQUID SAMPLING

(71) Applicant: Intellicyt, Albuquerque, NM (US)

(72) Inventors: Stephen M. Barnes, Albuquerque, NM (US); Aaron B. Kennington, Albuquerque, NM (US)

(73) Assignee: Intellicyt, Albuquerque, NM (US)

( * ) Notice: Subject to any disclaimer, the term of this patent is extended or adjusted under 35 U.S.C. 154(b) by 238 days.

(21) Appl. No.: 14/798,115

(22) Filed: Jul. 13, 2015

(65) Prior Publication Data

US 2016/0011083 A1    Jan. 14, 2016

Related U.S. Application Data

(60) Provisional application No. 62/023,778, filed on Jul. 11, 2014.

(51) Int. Cl.
  *G01N 35/00*    (2006.01)
  *G01N 35/10*    (2006.01)

(52) U.S. Cl.
  CPC ................... *G01N 35/1011* (2013.01)

(58) Field of Classification Search
  CPC .................................................. G01N 35/1011
  USPC ........................ 33/717–719; 422/105, 62, 83
  See application file for complete search history.

(56) References Cited

U.S. PATENT DOCUMENTS

| 4,140,018 | A | * | 2/1979 | Maldarelli | G01N 35/00 73/863.11 |
|---|---|---|---|---|---|
| 6,270,726 | B1 | * | 8/2001 | Tyberg | G01N 35/1011 422/509 |
| 7,842,244 | B2 | * | 11/2010 | Sklar | G01N 35/085 422/403 |
| 8,050,802 | B2 | * | 11/2011 | Young | B82Y 35/00 250/442.11 |
| 8,647,594 | B2 | * | 2/2014 | Kehrer | G01N 35/04 422/501 |
| 9,255,939 | B2 | * | 2/2016 | Nishida | G01N 35/1011 |
| 2005/0042138 | A1 | * | 2/2005 | Ueda | B01L 3/50825 422/63 |
| 2005/0250173 | A1 | * | 11/2005 | Davis | G01N 35/028 435/29 |
| 2011/0223061 | A1 | * | 9/2011 | Oonuma | G01N 35/10 422/62 |
| 2012/0222773 | A1 | * | 9/2012 | Yamato | G01N 35/10 141/1 |
| 2013/0205920 | A1 | * | 8/2013 | Tow | B29C 67/0074 73/863.01 |

(Continued)

*Primary Examiner* — Christopher Fulton
(74) *Attorney, Agent, or Firm* — McDonnell Boehnen Hulbert & Berghoff LLP

(57) ABSTRACT

An apparatus and method for detecting microplate well surface contact and setting standoff is provided. The apparatus may include a sample probe, coupled to a spring-loaded carriage, and a sensor configured to detect when the sample probe is in contact with a surface. The sample probe is moved toward a surface of a well in a well-plate until the sample end of the sample probe contacts the surface, whereby the carriage allows the probe to be displaced. Displacement of the probe is detected by the sensor and further downward movement of the carriage is stopped. A processor records the location of the sample probe and sets standoff based on the recorded location.

20 Claims, 5 Drawing Sheets

(56) References Cited

U.S. PATENT DOCUMENTS

2015/0185243 A1* 7/2015 Quarre ............... G01N 35/1009
422/509

\* cited by examiner

FIGURE 1

CONTACT SENSING PROBE AND METHODS OF USE FOR MICROPLATE LIQUID SAMPLING

CROSS-REFERENCE TO RELATED APPLICATIONS

This application claims priority to U.S. Provisional Application No. 62/023,778 filed Jul. 11, 2014, which is hereby incorporated by reference in its entirety.

BACKGROUND

In typical flow cytometry sampling systems, microplate well-depth variation, mechanical inaccuracies within the sampling system, including assembly tolerance stack up and surface flatness variations, may affect repeatability and consistency of sample collection. In particular, these issues may cause the sample probe of the system to make contact with the bottom or other surface of a sample well, which may be undesirable. Contacting the sample well surface during sampling can restrict fluid uptake. Yet, it is typically desirable to sample very close to the bottom of a well. Further, user-dependent calibration of the system can lead to inconsistency in operation of the system.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively.

The description of embodiments of the disclosure/examples is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All embodiments of any aspect of the invention can be used in combination, unless the context clearly dictates otherwise.

SUMMARY

Methods and apparatuses for detecting contact of a sample probe with a surface are disclosed herein.

Embodiments of the present disclosure provide a sampling apparatus, comprising: (1) a linear mechanical drive; (2) a carriage coupled to the linear mechanical drive; (3) a probe holder coupled to the carriage; (4) a sample probe coupled to the probe holder wherein the sample probe has a sample end and an indicator end; (5) a sensor configured to detect contact of a sample end of the sample probe with a surface; and (6) a processor configured to communicate with the sensor.

Further embodiments of the present disclosure provide a method for detecting surface contact of a sample probe, comprising: (a) providing the apparatus of claim 1; (b) moving, via the processor, the carriage and the sample probe toward a surface of a well in a well-plate until the sample end of the sample probe contacts the surface; (c) displacing the sample probe with respect to the carriage; (d) detecting, via the sensor, contact of the sample end of the sample probe with the surface; (e) stopping, via the processor, the movement of the carriage; and (f) recording, via the processor, a contact location of the sample probe.

Some embodiments of the present disclosure provide a method for detecting surface contact of a sample probe, comprising: (a) driving a sample probe toward a surface at a first speed, via a linear mechanical drive; (b) detecting, via a sensor, contact between the sample probe and the surface; (c) stopping motion of the sample probe, via the linear mechanical drive; (d) driving the sample probe away from the surface at a second speed, via the linear mechanical drive, until contact between the sample probe and the surface of a well is no longer detected, wherein the first speed is greater than the second speed; and (e) recording, via a processor, a location of the contact of the sample probe.

Still further embodiments of the present disclosure provide a method for detecting surface contact of a sample probe, comprising: driving, via a linear mechanical drive, a sample probe to a default contact location; and either and (i) in response to the sample probe contacting a surface at the default contact location: moving the sample probe, via the linear mechanical drive, away from the surface until contact with the surface is not detected; and recording a location of contact with the surface; or (ii) in response to the sample probe not contacting the surface at the default contact location: moving, the sample probe, via the linear mechanical drive, toward the surface until contact with the surface is detected; and recording the location of contact with the surface.

BRIEF DESCRIPTION OF THE DRAWINGS

FIG. 1 is a chart presenting example measurements taken from a 96-well microplate.

DETAILED DESCRIPTION

Methods and devices for accurately positioning a liquid sampling probe inside microplate wells are described herein. Exemplary screening systems use a hypodermic tube-sized sample probe to aspirate liquid out of microplate wells so that a liquid sample stream can be analyzed by flow cytometry. When the system is aspirating the sample liquid out of the wells (sampling), the location of the probe relative to the bottom of the well is one factor that may affect accurate and repeatable sampling. The described sampling system measures the location of the bottom of the well so that the system can accurately position the probe relative to the bottom of the well. In some examples, the method used to measure the location of the bottom of the well comprises the probe making physical contact with the well bottom. The method may also be used for other applications such as virtually levelling the surface on which the microplate is positioned, such as a shaker deck, setting the height of the sample end of the sample probe with respect to the wells of a microplate, mapping the position and depth of every well in a microplate, virtually levelling microplates, detecting unexpected contact, verifying expected contact, checking whether a container is closed or open, detecting if a microplate is in place in the system, setting sampling height in real time, locating the well or other surface details in the horizontal plane by using repeated height measurements with varying horizontal position offsets, etc.

A. Overview

In some embodiments of the present invention, the sampling system determines the depth of the sample end of the sample probe within a microplate well when the sample probe is inserted into the well to aspirate a well sample. The deeper the sample probe is inserted into the well, the deeper it is immersed in the fluid in the well and the closer the sample end of the sample probe gets to the bottom of the well. This distance from the bottom of the well to the sample end of the sample probe is called the standoff. At one extreme, the sample probe may be inserted into the well so far that it comes into contact with the bottom of the well; this is also known as zero standoff.

Figure 1:
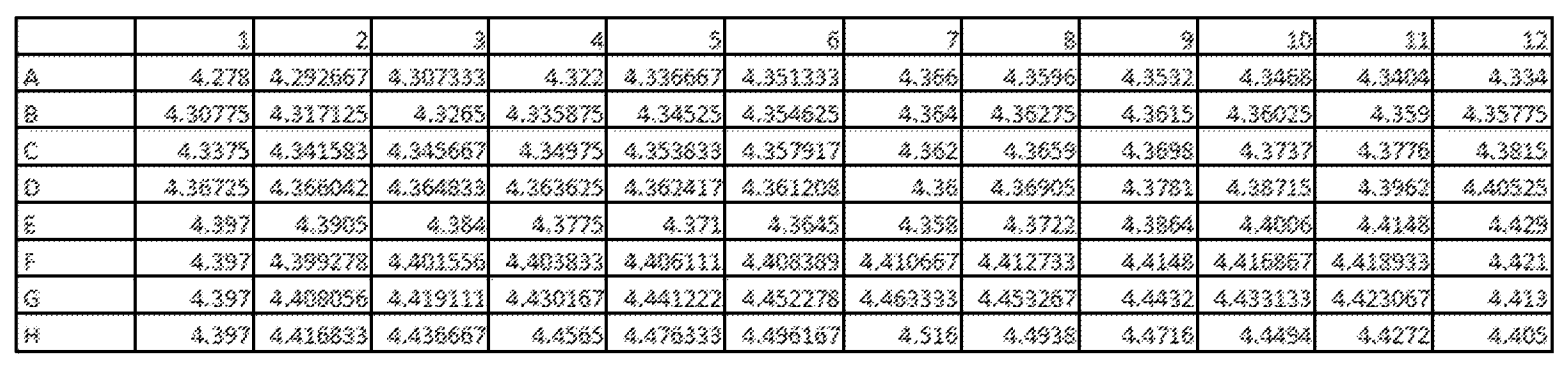
Figure 2:
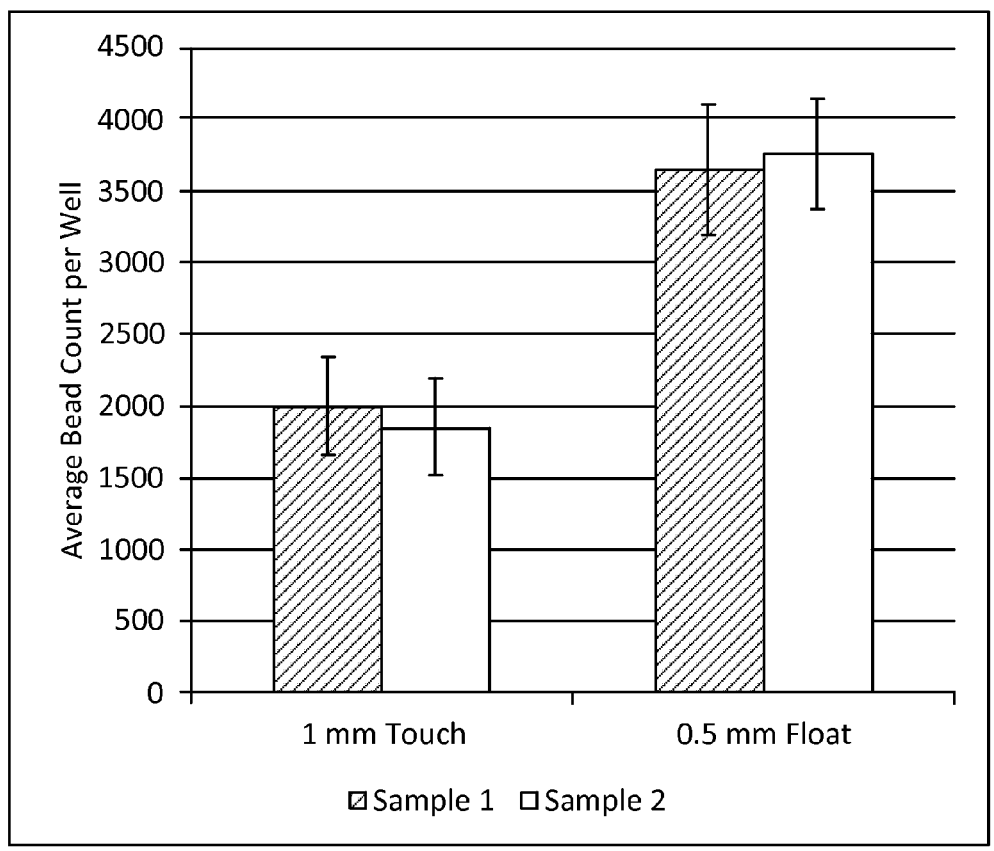
FIG. 2 is a graph illustrating sample uptake restriction when a sample probe touches the bottom of a sample well.

It has been measured and determined that some microplates exhibit a variation in the depth of the bottom of wells on the order of 0.75 mm or more from the low point on a microplate to its high point. For example, FIG. 1 presents example measurements taken from a 96-well microplate, illustrating Z-height variation among the wells. The numeric values in each cell of the chart represent the difference between the measured Z-height of each well and the previously-measured height of the shaker deck below each well in millimeters. The measurements show local Z-height variation as well as a general trend for the measured microplate. A single standoff may not adjust for this variation in depth. In operation, it is desirable to sample very close to the bottom of a well. Often, the standoff of the system may be set to less than 1 mm in order to achieve this. However, with such a close standoff, the large depth variation of 0.75 mm across the wells of the microplate, and depending on which well is used to set the standoff, it is possible that the sample probe may come into contact with the bottom of the well during sampling. As shown in FIG. 2, this may be undesirable because it can restrict fluid uptake during sampling. FIG. 2 illustrates the results of an experiment where 1536-microplates were filled with fluorescent beads and sampled using the example sampling systems disclosed herein. For the "0.5 mm Float" samples, the sample probe was set to a standoff of 0.5 mm or more.

In addition to the microplate well-depth variation, mechanical inaccuracies within the sampling system, including assembly tolerance stack up and surface flatness variations, may affect the measurement of the bottom of the wells. One source of mechanical inaccuracy may be the sample probe itself, which may vary in length. This may be important because the sample probe is a fragile consumable that a system user changes on a periodic basis. Movement of the probe holder may also be unconstrained. In addition to the variations in the sampling system, which may be controlled, there is also variation in the microplates, which cannot be easily controlled. For example, there may be microplate to microplate variation, injection mold variation, manufacturing lot to lot variation, etc. If used, microplate shaker grippers, which hold a microplate in place on a shaker, can also warp the plates enough to distort the depth of the wells with respect to the sample end of the sample probe.

B. Example Systems

U.S. Pat. No. 7,842,244, the entire contents of which are incorporated by reference herein, describes a flow cytometry apparatus for high throughput screening by the detection of particles from a plurality of samples. As generally described therein, a flow cytometry apparatus may include an autosampler having an adjustable sampling arm, to which a sampling probe is mounted. The sampling arm is capable of moving within the X, Y and Z directions to be lowered into individual sample wells of a sample plate to obtain a sample that has, for example, been tagged with a fluorescent tag to be analyzed using the flow cytometry apparatus. Once a sample is picked up by the probe, a peristaltic pump forces the sample through a tube that extends from the autosampler through the peristaltic pump and into a flow cytometer including a flow cell and a laser interrogation device. The laser interrogation device examines individual samples flowing from the flow cell at a laser interrogation point. When samples pass through the laser interrogation point, the particles in the samples are sensed by flow cytometer due to the fluorescent tag on the particles.

Figure 3:
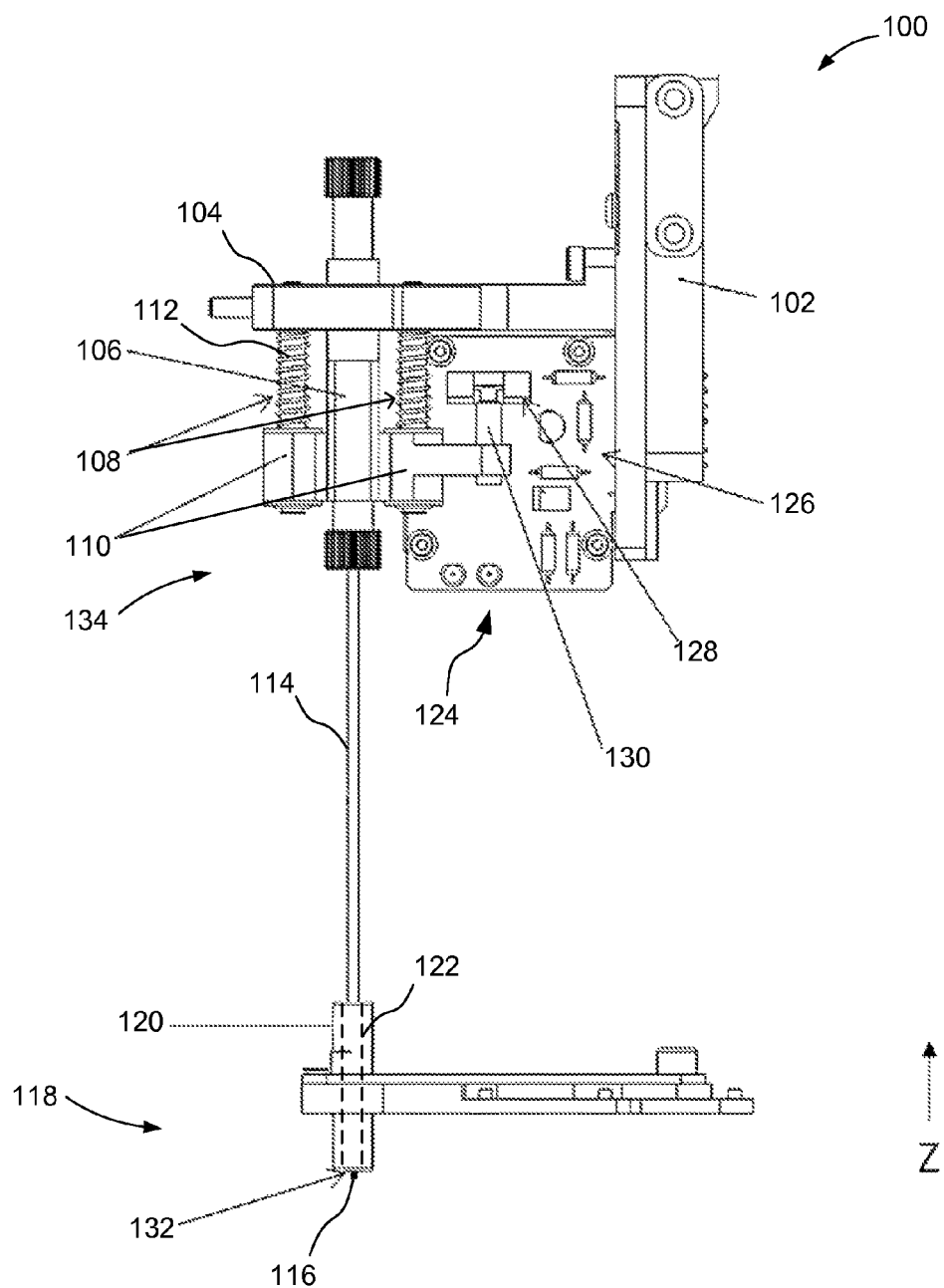
FIG. 3 illustrates a side view of an example sampling system.
Figure 4:
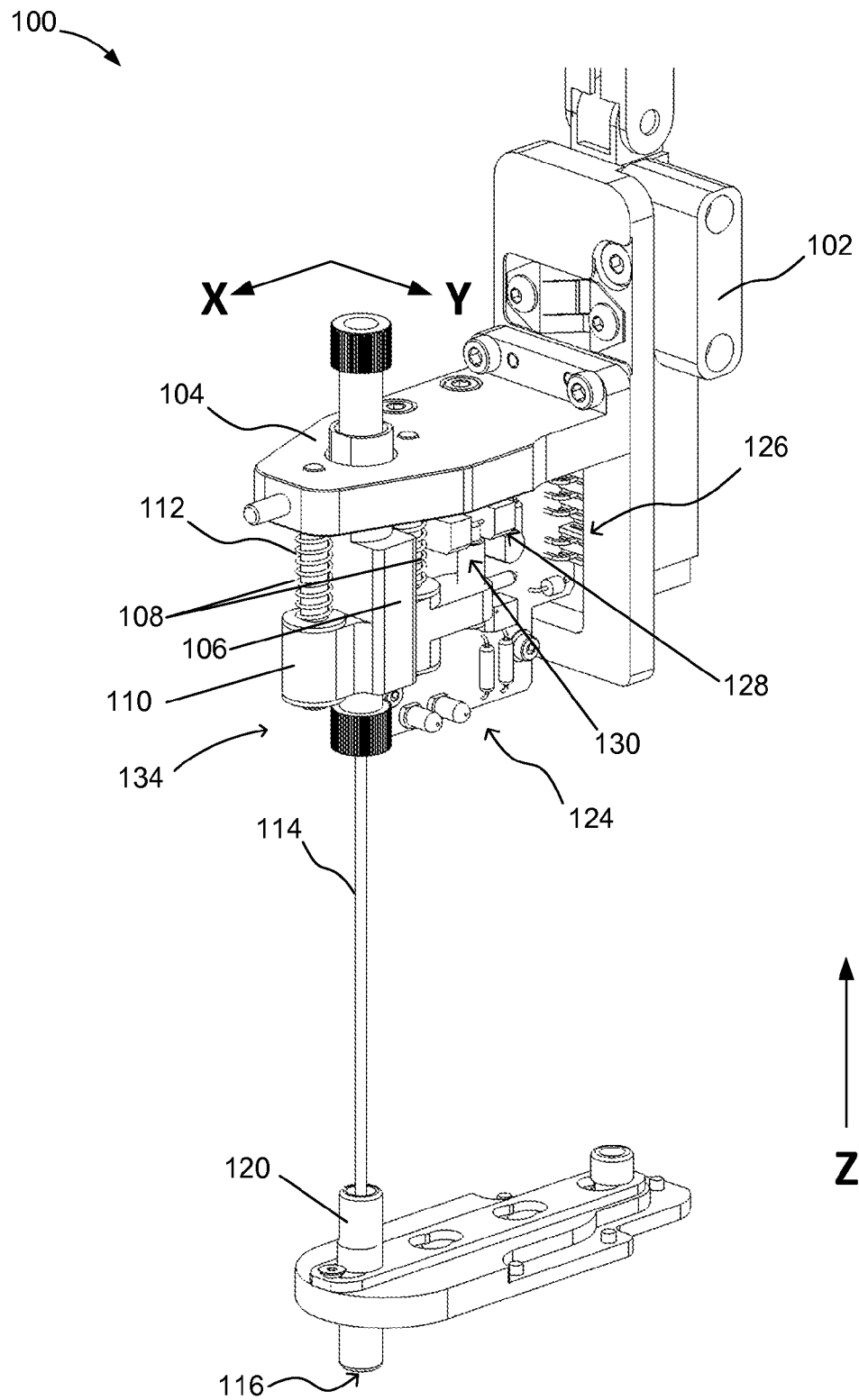
FIG. 4 illustrates a perspective view of the example sampling system of FIG. 3.

FIGS. 3 and 4 illustrate an example sampling system 100 for use with a flow cytometer (not shown), such as that described in U.S. Pat. No. 7,842,244. The sampling device of the high throughput apparatus includes a Carriage 102 that is coupled to and movable by a vertical linear mechanical drive (not shown). A Probe Holder 106 may be connected to a sampling arm 104 of the Carriage 102 by two spring-loaded vertical shafts 108, slidably disposed within Guides 110. Sampling arm 104 defines an X-Y plane (see FIG. 4). In one example, sampling arm 104 extends substantially perpendicular from the Carriage 102. The vertical shafts 108 allow the Probe Holder 106 to be displaced in the Z-direction, with respect to the Carriage 102, between an undisplaced position and at least one displaced position. To prevent undesired motion, two Compression Springs 112 may apply a force which biases the Probe Holder 106 in the undisplaced position (shown undisplaced in FIGS. 3 and 4). In this embodiment, the two Compression Springs 112 are compressed when the Probe Holder 106 is in a displaced position. The Probe Holder 106 may be coupled to the Carriage 102 by any restorative force mechanism, including, but not limited to, gravitational, magnetic, elastomeric, or pneumatic mechanisms or other mechanical spring types.

The Probe Holder 106 is coupled to an Outer Probe 114 and a Sample Probe 116, slidably disposed therein. The Sample Probe 116 has a sample end 132 and an indicator end 134 opposite thereof. The sample end 132 of the Sample Probe 116 is positioned at a distal end 118 of the system 100, nearest to where a microplate containing sample wells may be positioned during sampling. The Sample Probe 116 conveys the sample out of the wells, via a sample end 132, and into the sample tubing of the flow cytometer (not shown). The Sample Probe 116 may be coupled to the Probe Holder 106 at or near the indicator end 134.

A Probe Guide 120, positioned at the distal end 118 of the system 100, slidably receives the Outer Probe 114 within channel 122. The Outer Probe 114 keeps the Sample Probe 116 in position by sliding through the Probe Guide 120. Probe Guide 120 does not move in the Z-direction and constrains X-Y motion of the Sample Probe 116. As the Sample Probe 116 is coupled to the Probe Holder 106, the Sample Probe 116 is also displaceable in the Z-direction relative to the Carriage 102 between an undisplaced position and at least one displaced position.

To sense displacement of the indicator end 134 of the Sample Probe 116 and, therefore, Probe Holder 106 with respect to the Carriage 102, the system 100 may include a sensor 124 configured to detect when a sample end 132 of the Sample Probe 116 is in contact with a surface for example, the bottom of a sample well. In the embodiment shown in FIGS. 3 and 4, the sensor 124 may include a Circuit Board 126 with a Photo Interrupter 128 and other electrical components coupled to an indicator end 134 of the Sample Probe 116, via the Probe Holder 106. The Circuit Board 126 may power the Photo Interrupter 128 and provide communication with a processor. When the Sample Probe 116 and Probe Holder 106 are displaced by contact into a displaced position, a Calibration Screw 130 positioned on the Probe Holder 106 moves into the light beam of the Photo Interrupter 128. When the light beam of the Photo Interrupter 128 is interrupted, a signal is generated by the Circuit Board 126 and sent to a processor running control software for analysis.

The sensor 124 may be provided as any device capable of sensing when the indicator end 134 of the Sample Probe 116 and, therefore, Probe Holder 106 is in a displaced position. For example, the sensor 124 may be a laser, a microswitch, a magnet, a capacitor, a linear variable differential transformer, a string or linear potentiometer, a strain gauge, a surface acoustic wave sensor, a temperature sensor, a micro-electro-mechanical system or a reed gage. In one example, the Outer Probe 114 or the Sample Probe 116 may be electrically connected to a circuit and displacement thereof could create a connection, for example via the indicator end 134 of the Sample Probe 116, to complete an electrical circuit, thereby allowing a detectable current to flow. Broadly, the Inner Probe 116, Outer Probe 114, or Probe Holder 106 could be an element in an electrical switch. In further embodiments, contact sensing does not require Sample Probe 116 displacement to detect contact of the Sample Probe 116. The sensor 124 could detect changes in the Sample Probe 116 capacitance as the sample end 132 of Sample Probe 116 comes into contact with a surface. The sensor 124 could be a strain gauge that detects compression of the Sample Probe 116 when the sample end 132 is in contact with a surface. Alternatively, the Sample Probe 116 could be vibrated in the direction of the Z-axis by a piezoelectric actuator which is running at resonance. When the sample end 132 of the Sample Probe 116 contacts a surface, the sensor 124 could detect the change in current the actuator experiences when the resonance changes. This could be implemented with a surface acoustic wave sensor. The sensor 124 could alternatively be provided as a temperature sensor that would detect when the Sample Probe 116 has contacted a surface having a different temperature from the Sample Probe 116. In another embodiment, the sensor 124 could be a pressure or contact sensor attached to the sample end 132 of the Sample Probe 116. The sensor 124 could also be a MEMS device. In this example, the MEMS device could be the surface acoustic wave sensor, strain gauge, temperature sensor, or pressure sensor, etc.

In other embodiments, a plurality of parallel contact sensing probes coupled to the Probe Holder 106 may be used to increase overall sampling throughput, with each individual Sample Probe 116 sampling from a separate well. Each Sample Probe 116 could be on a separate Z-axis or each Sample Probe 116 could be on a secondary adjustment axis that allows fine tuning of its particular Z-position.

Figure 5:
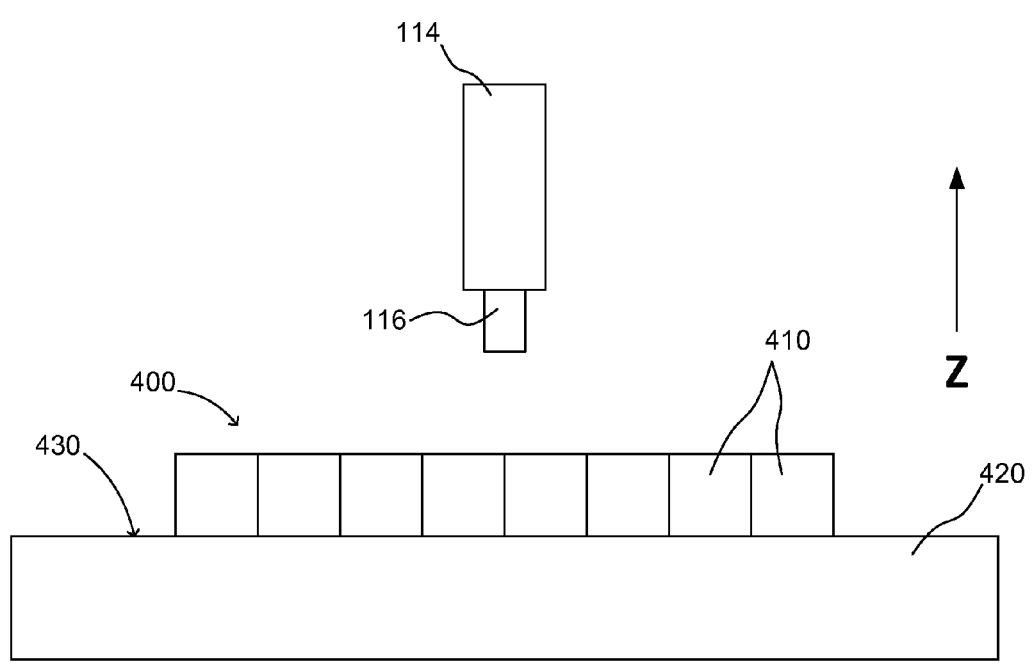
FIG. 5 is a schematic illustration of a portion of a sampling system in proximity to a microplate well.

In addition to setting standoff, the sensor 124 of the system 100 may also be used to make a number of other measurements and determinations to improve sampling consistency and repeatability. For example, it is desirable that the X-Y plane defined by the sampling arm 104 be parallel to a plane defined by the surface on which the sample microplate is positioned. In some examples, the microplate may be positioned on the deck, or top surface, of a shaker configured to agitate the microplate during sampling. Alternatively, in some cases, the sample microplate may be placed on a fixed deck. The sample microplate may also be presented to the sampler by a robot arm. System 100 may be used to correct for a difference in orientation between the plane of the sampling arm and the plane defined by the surface on which the microplate is positioned. FIG. 5 is a schematic illustration of a microplate 400, including a number of wells 410, positioned on a shaker 420. Deck height is the Z-height of the sample end 132 of the Sample Probe 116 when it is touching the surface on which the microplate is positioned, such as the shaker deck 430. The shaker deck 430 is the top of the shaker 420 where the microplate 400 is held during sampling. The deck height is used as the base Z-height for the entire system and should be calibrated correctly for system accuracy. The sensor 124 can be used to automatically calibrate deck height and do it more accurately and precisely than a user can.

The sensor 124 may also be used to verify correct installation of the Sample Probe 116 on the system 100 by measuring the location of a reference surface. In some examples, the reference surface may be the shaker deck, but any other fixed surface could be used. If the measurement is not within acceptable limits, the system 100 can report the problem to the user and recommend actions to fix the problem.

Because of mechanical variability in the assembly of the sampling system 100, the plane of the shaker deck 430 may not be perfectly parallel to the XY plane of the sampling arm 104. By measuring the Z-height of 3 or more points on the shaker deck 430, the processor can determine the plane of the shaker deck 430 relative to the sampling arm 104. The three points can each correspond to separate wells 410 of the well plate 400. Using that information, a processor, executing software, can determine a plane of the shaker deck relative to the sampling arm. The processor can actively adjust sampling standoff for a plurality of wells 420 based on the plane of the shaker deck 430 to compensate for any non-parallelism with respect to the sampling arm 104.

Repeatability data collected using the present system for over 10,000 contact measurements of one point shows a standard deviation of 0.028 mm. The example systems disclosed herein may improve the repeatability and consistency of the data produced by sampling systems. The repeatability is improved due to the precise and controlled sampling height that can be achieved. The consistency is improved because calibration is automatic and is no longer user dependent.

C. Example Methods

Example methods for operating a sampling system are also disclosed herein. Any of the example systems, including system 100, described above with respect to FIGS. 2, 3, and 4 may be used to carry out the example methods.

In a first example method, a processor configured to operate system 100, moves Carriage 102 and a Sample Probe 116 toward a surface of a well in a well-plate until the sample end 132 of the Sample Probe 116 contacts the surface. The sensor 124 senses contact of the sample end 132 with the surface and generates a signal that is transmitted to the processor, which ceases movement of the Carriage 102. A contact location, which may be a Z-height, of the Sample Probe 116 is recorded. A Z-height is determined with respect to the surface on which the microplate is positioned, such as a shaker deck. The contact location may also include a location within the X-Y plane defined by the microplate. For example, the contact location may indicate the location of a wall between individual wells.

In one example, contact between the sample end 132 of the Sample Probe 116 and the surface is determined by detecting the indicator end 134 of the Sample Probe 116 by the sensor 124. Contact of Sample Probe 116 with the well causes displacement of the Probe Holder 106 and the indicator end 134 of the Sample Probe 116, with respect to the Carriage 102, into a displaced position. In the displaced position, the indicator end 134 of the Sample Probe 116 may be detected by a sensor 124. Upon detection of an indicator end 134 of the Sample Probe 116, the sensor 124 generates a signal that is sent to a processor, via an electrical connection to the Circuit Board 126, which stops the movement of the Carriage 102. A contact location of the Sample Probe 116 is recorded by the processor. In one example, the indicator end 134 of the Sample Probe 116 may be detected by moving a calibration screw coupled to the indicator end 134 of the Sample Probe 116 into a light beam of a photo interrupter. A signal generated by the sensor 124 on the Circuit Board 126 is sent to the processor. A second contact location of a second surface may also be determined by the system 100.

The hardware of system 100 and the software and any other components that control the movement of the Carriage 102 and sampling arm 104 may make up a sampling control system. For example, the software may include program instructions for causing the linear mechanical drive to move the Carriage 102 as described herein. The software of the sampling control system may also include instructions for determining contact locations and setting standoff as described herein. Further, the software may include program instructions for controlling operations of the flow cytometer, including operating the sampling pump. The processor as described herein may communicate signals generated by the sensor 124 to the sampling control system.

The standoff determination made by the sampling control system may be used to operate the sampling system 100 in a number of ways. In one embodiment, with the contact sensor 124 in place, the sampling system 100 can actively set the standoff during microplate well sampling, in real-time. For each well, the sampling system 100 measures the location of the bottom of a well 410 and then raises the Sample Probe 116 to the desired standoff. In operation, the Sample Probe 116 is lowered into the well 410 until it contacts the bottom of the well. The Sample Probe 116 is raised to the desired standoff and the desired amount of sample liquid is sampled from the well 410. The sampling pump of the flow cytometer (not shown) could be running continuously at the beginning of sampling, or it could be turned on to begin sampling. The Sample Probe 116 is then withdrawn from the well 410. Using this method, the system can compensate in real-time for any variation in the location of the bottom of the wells without having to map the microplate wells before sampling.

However, in some cases, operating the system 100 by calculating standoff in real-time may not be desired because the Sample Probe 116 must contact the bottom of the well in real-time mode. For example, there may be assays that cannot allow the Sample Probe 116 to contact the bottom of the well or move that far into the well. In addition, the measurement of the bottom of the well can be relatively slow compared to open-loop sampling.

Alternatively, the sampling system 100 can measure all or a sub-sample of microplate well depths before an experiment is run for the given type of microplate. An empty microplate would be loaded and the system 100 would measure the well Z-height for the set of wells. Once the microplate well depth map has been created, microplate(s) with the actual samples are loaded, and the sampling system would use microplate well depth map to position the sample end 132 of the Sample Probe 116 to correct standoff for each microplate well.

For high-density microplates, like 384-well and 1536-well microplates, learning each well may be time consuming. In some cases, sampling a 1536-well microplate can take over an hour. To reduce the time to map the wells, the system 100 can sample a subset of the microplate wells. The subset of wells of the well depth map can used to interpolate the well depths of wells not directly measured. This concept can be used for any subset of the wells from the full count down to two wells. Further, this concept can be used for both well-mapping and for real-time standoff calculation.

In addition, the contact sensor 124 can be used to calculate the X-Y location of one or more wells. To do this, the sampling system 100 would map the Z values at contact for an area in X-Y that covers some portion of the well walls. The area map would then be used to calculate the location of the well walls, and from there, the center of the well can also be calculated.

Once a well map is created, during well depth mapped sampling, the Sample Probe 116 does not make contact with any surface. Contact with a surface would be interpreted as a sampling error. For instance, if the Sample Probe 116 contacted the edge of a well wall, a sampling error would have occurred. The sampling system 100 can monitor the contact sensor during sampling to ensure no contact is made. If contact is made, the system 100 could handle the error in various ways including warning the user, stopping the experiment, logging the contact in the experiment database, etc.

The reverse is also potentially possible: in some experiments, contact with the bottom of the wells may be desired. In such experiments, the system 100 could monitor the contact sensor 124 and if contact was not made when contact was expected, the lack of contact is reported as an error.

To obtain the most accurate Z-height measurement at contact, the Sample Probe 116 may be moved slowly into contact with a surface. This slow movement may reduce the overshoot of the Carriage 102 after the contact sensor 124 has tripped and the linear drive is commanded to stop. However, reducing the Z-axis speed while contact sensing can increase the time required to take Z-height measurements. To alleviate this, the contact sensor 124 and Z-height measurement functions can be separated. Contact sensing may be done quickly and then Z-height measurements may be done more slowly afterward. In an example process, the linear drive drives the Sample Probe 116 toward the surface at a first speed until contact is sensed. The linear drive decelerates the Sample Probe 116 to a stop and then drives the Sample Probe 116 upward at a second speed until contact is not sensed, where the first speed is greater than the second speed. The Z-height of the sample end 132 of the Sample Probe 116 is recorded as the contact location.

In one example, the first, or fast, speed may be 100 mm/s and the second. The second, or slow, speed may be 40 mm/s. In some cases, where the Sample Probe 116 moves only a short distance, the probe may not have sufficient space or time to reach a target "fast" or "slow" speed. For example, when the Sample Probe 116 moves away from contact with the surface, the Sample Probe 116 may reach only 10 mm/s.

In some cases, a well may have a default contact location. Generally, if the surface location is known, the Carriage 102 drives the Sample Probe 116 to the default, known location. The contact sensor 124 is monitored. If contact is sensed at the default location, the Carriage 102 moves the Sample Probe 116 away from the surface until contact is not sensed and the Z-height is recorded. If contact is not sensed at the default location, the Sample Probe 116 moves toward the surface until contact is sensed and the Z-height is recorded. In one embodiment, a more rapid process can be employed. First, the axis drives the Sample Probe 116 as rapidly as possible to the expected location. For example, the Sample Probe 116 may move at approximately 100 mm/s to the expected location. If the Sample Probe 116 impacts the surface, the spring-loaded Carriage 102 allows the Sample Probe 116 to move with the Probe Holder 106 and damage is prevented. If contact was not sensed at the default location, the Sample Probe 116 moves slowly toward the surface until contact is sensed and the Z-height is recorded. If contact was sensed at the default location, the Carriage 102 moves the Sample Probe 116 slowly away from the surface until contact is not sensed and the Z-height is recorded. "Slowly" may be approximately 10-40 mm/s.

In some cases, a lid, foil seal, or other cover may be placed over a microplate to, for example, prevent sample evaporation or contamination. As sampling 1536-well microplates can require over an hour to sample all the microplate wells, the liquid in the wells can evaporate enough during sampling to negatively affect the experiment. In this case, it may be desirable to seal the top of the microplate. The contact sensing Sample Probe 116 can be used to pierce through the seal and pass into the well. The seal could be attached with a thermal, ultrasonic, adhesive, contact pressure, or other process. The seal could be made of metal, plastic, or any other material as long as it can be pierced by the Sample Probe 116. To facilitate piercing, the seal material can be pre-scored or cut. In some examples, the sample end 132 of the Sample Probe 116 can be shaped or sharpened to facilitate piercing.

The contact sensor 124 could also be used to detect the presence of a seal or any other covering, or if a consumable cartridge is opened or closed. Consumable cartridges or other liquid containers can be used by the sampling system to clean, rinse, or flush the probe before or after sampling from a well or microplate. If contact is made, the system 100 could handle the error in various ways including warning the user, stopping the experiment, logging the contact in the experiment database, etc.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:
1. An apparatus, comprising:
a linear mechanical drive;
a carriage coupled to the linear mechanical drive;
a probe holder coupled to the carriage;
a sample probe coupled to the probe holder wherein the sample probe has a sample end and an indicator end, wherein the sample probe is moveable relative to the carriage between a first undisplaced position and a second displaced position and wherein the sensor is configured to detect the sample probe in the second displaced position;
a calibration screw coupled to the indicator end of the sample probe;
a sensor configured to detect contact of a sample end of the sample probe with a surface; and
a processor configured to communicate with the sensor.
2. The apparatus of claim 1, wherein the probe holder is coupled to the carriage by two spring-loaded vertical shafts.
3. The apparatus of claim 1, wherein the probe holder is coupled to the carriage by a restorative force mechanism.

4. The apparatus of claim 1, further comprising:
an outer probe coupled to the probe holder; and
a probe guide defining a channel configured to slidably receive the outer probe.
5. The apparatus of claim 4, wherein one or more of the sample probe, the outer probe and the probe holder are electrically conductive and are configured to complete an electrical circuit when the sample probe is in the second displaced position, and wherein the sensor is configured to detect completion of the electrical circuit.
6. The apparatus of claim 1, wherein the sensor comprises a photo interrupter, and wherein when the sample probe is in the second displaced position, the calibration screw is configured to be disposed in the path of a light beam from the photo interrupter.
7. The apparatus of claim 1, wherein the sensor is selected from the group consisting of: laser, a microswitch, a magnet, a capacitor, a linear variable differential transformer, a string or linear potentiometer, a strain gauge, a surface acoustic wave sensor, a temperature sensor, a micro-electro-mechanical system and a reed gage.
8. The apparatus of claim 1, wherein the sensor is configured to detect a change in capacitance of the sample probe when the sample end of the sample probe is in contact with a surface.
9. The apparatus of claim 1, wherein the sensor comprises a strain gauge configured to detect compression of the sample probe when the sample end of the sample probe is in contact with a surface.
10. The apparatus of claim 1, further comprising a plurality of parallel contact sensing probes coupled to the probe holder and arranged to sense contact of each of the sensing probes in separate wells, wherein standoff comprises a distance between the surface and each of the sensing probes.
11. A method, comprising:
providing the apparatus of claim 1;
moving, via the processor, the carriage and the sample probe toward a surface of a well in a well-plate until the sample end of the sample probe contacts the surface;
displacing the sample probe with respect to the carriage;
detecting, via the sensor, contact of the sample end of the sample probe with the surface;
stopping, via the processor, the movement of the carriage; and
recording, via the processor, a contact location of the sample probe.
12. The method of claim 11, wherein detecting contact of the sample end of the sample probe with the surface comprises:
moving a calibration screw coupled to the indicator end of the sample probe into a light beam of a photo interrupter;
generating a signal, via a circuit board coupled to the photo interrupter; and
sending the signal, via the circuit board, to a sampling control system.
13. The method of claim 11, further comprising:
determining, via the sensor, a second contact location of a second surface.
14. The method of claim 11, further comprising:
measuring, via the sensor, at least three contact locations each corresponding to a respective well of the well-plate;
determining, via the processor, an orientation of a plane defined by a surface on which the well plate is positioned relative to a plane defined by a sampling arm extending from the carriage, and wherein the probe holder is coupled to sampling arm.

15. The method of claim 14, further comprising:
adjusting, via the processor, standoff for a plurality of wells of the well-plate based upon the orientation of the plane defined by the surface on which the well plate is positioned, wherein the standoff comprises a distance between a contact location and the sample end of the sample probe.

16. The method of claim 11, further comprising:
after the sample end of the sample probe contacts the surface of a well, raising the sample probe to a desired standoff, wherein the standoff comprises a distance between a contact location and the sample end of the sample probe;
sampling an amount of liquid from the well; and
withdrawing the sample probe from the well.

17. A method, comprising:
driving a sample probe toward a surface at a first speed, via a linear mechanical drive;
detecting, via a sensor, contact between the sample probe and the surface;
stopping motion of the sample probe, via the linear mechanical drive;
driving the sample probe away from the surface at a second speed, via the linear mechanical drive, until contact between the sample probe and the surface is no longer detected, wherein the first speed is greater than the second speed; and
recording, via a processor, a location of contact of the sample probe.

18. The method of claim 17, wherein the first speed is 100 mm/s.

19. The method of claim 18, wherein the second speed is 40 mm/s or less.

20. A method, comprising:
driving, via a linear mechanical drive, a sample probe to a default contact location; and either:
(a) in response to the sample probe contacting a surface at the default contact location:
moving the sample probe, via the linear mechanical drive, away from the surface until contact with the surface is not detected; and
recording a location of contact with the surface; or
(b) in response to the sample probe not contacting the surface at the default contact location:
moving, the sample probe, via the linear mechanical drive, toward the surface until contact with the surface is detected; and
recording the location of contact with the surface.

* * * * *